United States Patent [19]

Harichian et al.

[11] Patent Number: 5,728,670

[45] Date of Patent: Mar. 17, 1998

[54] ENZYMATICALLY STABLE ALKYL (ALKYL GLYCOSID) URONATES AS NONIONIC SURFACTANTS AND A PROCESS FOR THEIR MANUFACTURE

[75] Inventors: Bijan Harichian, South Orange; Robert Vermeer, Nutley; Robert William Riley Humphreys, Annandale, all of N.J.

[73] Assignee: Lever Brothers Company, Division of Conopco, Inc., New York, N.Y.

[21] Appl. No.: 135,240

[22] Filed: Oct. 12, 1993

[51] Int. Cl.$^6$ .................................................. C11D 3/22
[52] U.S. Cl. .................... 510/392; 510/393; 510/226; 510/360; 510/305; 510/320; 510/321; 127/29; 127/30; 536/4.1; 536/123.1
[58] Field of Search ................... 127/29, 30; 536/4.1, 536/123.1; 252/174.17, 174.18; 510/392, 393, 226, 300, 305, 320, 321

[56] References Cited

U.S. PATENT DOCUMENTS

| | | |
|---|---|---|
| 2,562,200 | 7/1951 | Mehltretter . |
| 2,845,439 | 7/1958 | Reiners . |
| 5,342,929 | 8/1994 | Ernst et al. ................ 536/4.1 X |
| 5,356,883 | 10/1994 | Kuo et al. ................ 536/4.1 X |

FOREIGN PATENT DOCUMENTS

| | | |
|---|---|---|
| 0326673 | 12/1988 | European Pat. Off. . |
| 0427210 | 5/1991 | European Pat. Off. . |
| 3803465 | 2/1988 | Germany . |
| 93/02092 | 2/1993 | WIPO . |

*Primary Examiner*—Paul F. Shaver
*Attorney, Agent, or Firm*—Ronald A. Koatz

[57] ABSTRACT

Mixed chain alkyl (alkyl glycosid) uronates as nonionic surfactants are disclosed.

7 Claims, No Drawings

ENZYMATICALLY STABLE ALKYL (ALKYL GLYCOSID) URONATES AS NONIONIC SURFACTANTS AND A PROCESS FOR THEIR MANUFACTURE

FIELD OF THE INVENTION

This invention relates to mixed chain alkyl(alkyl glycosid)uronates as a new class of nonionic surfactants and a new process for their manufacture. The compounds of this invention were found to be unexpectedly stable to enzyme hydrolysis, which makes them especially suited for enzyme containing powdered and liquid detergent compositions.

BACKGROUND OF THE INVENTION

The demand for mild, environmentally friendly surfactants has been steadily rising. In general, most compositions contain surfactants based on petrochemicals. Since these materials often have handling, storage and environmental hazards associated with them, it would be most desirable to use surfactants which are instead derived from agriculturally grown materials, such as carbohydrates. These naturally occurring compounds represent a source of renewable raw materials that are readily available, inexpensive, biodegradable, aquatically favorable and optically pure.

It is well known that uronic acids and their lactones undergo many transformations when reacted with alcohols under acidic conditions. The major reactions which are thought to take place for D-glucurono-6,3-lactone and D-galacturonic acid are set forth below:

The Major Reactions of D-Glucurono-6,3-lactone With Alcohols

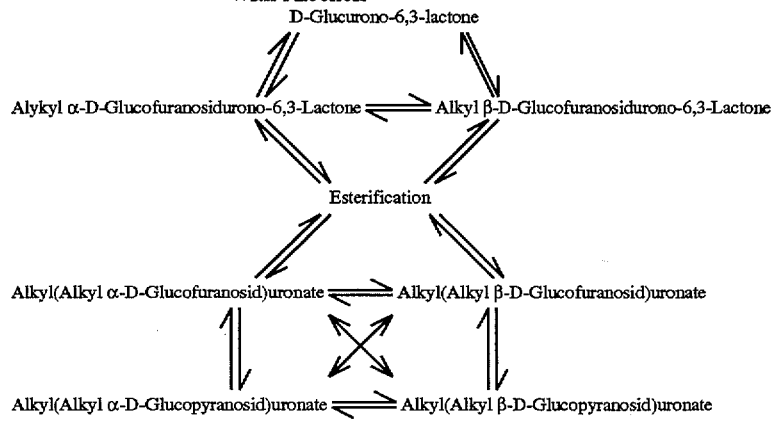

The Major Reactions of D-Galacturonic Acid with Alcohols

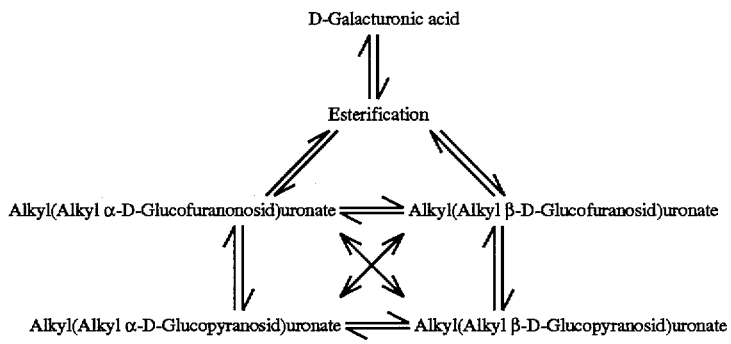

From the above schemes, it can be seen that with uronic acids (or their lactones), glycosidation and esterification are competing reactions resulting in a mixture of anomers. In the case of D-glucurono-6,3-lactone, glycosidation is more rapid than esterification, whereas the reverse holds true for D-galacturonic acid, esterification is more rapid than glycosidation.

This known method suffers from the distinct disadvantage of yielding dialkyl long chain (e.g., greater than 8 carbons) uronic acid esters that are not properly balanced and therefore, not suitable for providing surface activity. In this regard, it should be recalled that chain lengths necessary for effective surface activity generally range between 8 to 18 carbons total. Thus, when higher alcohols ($C_8$–$C_{18}$) are used according to the known method, the resulting uronic acid esters contain two long alkyl chains (dialkyl) generally having well over 30 carbons total and rendering them non-surface active.

We have developed a new method for preparing higher chain surface active alkyl(alkyl glycosid)uronates whose total number of alkyl carbons are between 8 and 18 which makes them well suited as balanced surfactants. The new method is based on selective alkaline transesterification of uronic acid at one reactive site whereas, the art known processes are based on random acidic esterification and glycosidation of uronic acid at two reactive sites.

Specifically, the alkyl(alkyl glycosid)uronates of the invention have one long alkyl group at the carboxyl site thereby rendering them properly balanced for effective surface activity. The invention can be more readily understood when reference is made to the following structures:

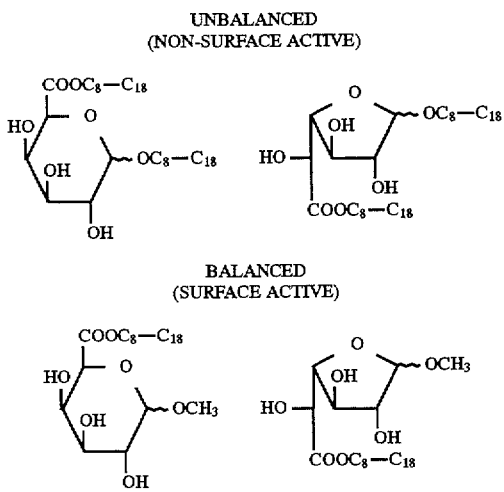

U.S. Pat. No. 2,562,200 to Mehltretter and U.S. Pat. No. 2,845,439 to Corn Products teach processes for preparing sodium(alkyl glycosid)uronates, but there is no such teaching or suggestion of the "balanced" molecules of the invention or that these molecules have the surfactancy advantage of the compound of the invention.

WO 93/02092 to Zschiminer & Schwarz teach galacturonic acid derivatives which are similar to the compounds of the invention; however, again there is no teaching in suggestion of using a "balanced" molecule having only one long chain ester such that total carbon number is suitable for surfactancy. In addition, there is no teaching of how such a compound could be made in any event.

In a copending application filed on the same date as this application, similar uronate compounds are taught except that in those compounds, the possible carboxyl site is simply a salt making them anionic in nature. The uronates of this invention are nonionic in nature.

Accordingly, it is one object of the invention to provide a novel detergent composition comprising of enzymatically stable alkyl(alkyl glycosid)uronate of the invention. Specifically, the alkyl(alkyl glycosid) uronates of the invention have only one long chain alkyl group and are well-suited as balanced surfactants.

Another object of the invention is to provide such a detergent composition which exhibits effective detergency and oily soil removal.

It is yet another object of the invention to provide a new process for the manufacture of surface active mixed chain alkyl(alkyl glycosid)uronates, preferably alkyl(methyl glycosid)uronates.

It is a particular object of the invention to prepare surface active mixed chain alkyl(alkyl glycosid)uronates in good yield, high purity, and desirable color without hydroxyl group protection, oligomerization or polymerization.

SUMMARY OF THE INVENTION

One embodiment of the invention relates to a novel detergent composition comprising surprising enzymatically stable surface active mixed chain alkyl(alkyl glycosid) uronate compounds, particularly, long chained alkyl(methyl glycosid)uronates derived from D-galacturonic acid. In this embodiment, only one of two possible reactive sites (carboxyl position) has a long chain alkyl group and the overall carbon count at both sites is perfectly balanced to effective surface activity.

The second embodiment of the invention relates to a new process for preparing such surfactants. The process is an improvement over the art known process for the preparation of unbalanced non-surface active uronic acid esters, wherein the improvement comprises selectively reacting a short chained non-surface active uronic acid ester directly with a long chained alcohol in the presence of an alkaline catalyst without requiring hydroxyl group protection and without oligomerization or polymerization. This embodiment is particularly directed to preparing balanced surface active mixed chain alkyl(alkyl glycosid)uronates in good yield, high purity and desirable color. The mixed chain alkyl(alkyl glycosid)uronates of the invention have detergency profiles equal to, or better than other well known nonionic surfactants based on petrochemicals, thereby indicating that they are viable, environmentally sound alternatives to traditional petrochemical surfactants.

DETAILED DESCRIPTION OF THE INVENTION

The present invention relates to a new class of environmentally friendly "green" nonionic glycolipid surfactants. In particular, the invention relates to balanced surface active alkyl(alkyl glycosid)uronates derived from D-galacturonic acid.

In one embodiment of the invention, novel detergent compositions comprising enzymatically stable mixed chain alkyl(alkyl glycosid)uronates are described.

In a second embodiment of the invention, a new process for the manufacture of balanced surface active mixed chain alkyl(alkyl glycosid)uronates are described.

In general, the mixed chain alkyl(alkyl glycosid)uronates of the invention are defined as glycosids of uronic acids, uronic acid salts or uronolactones of the following general formula:

Mixed Chain Alkyl(Alkyl glycosid)Uronate

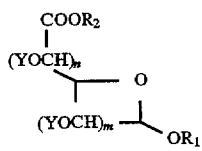

wherein:
n=0–2, preferably 0–1;
m=2–4, preferably 2–3;
Y is a hydrogen atom, mono-, oligo- or polysaccharide; uronic acid, uronic acid salt, uronolactone or polyuronic acid;
$R_1$ is hydrogen, a straight or branched chain alkyl group having 1 to 6 carbons, preferably 1 to 3 carbons or an alkenyl group with 2 to 6 carbons. $R_2$ is a straight or branched chain alkyl or alkenyl group which may contain an aromatic, cycloaliphatic, mixed aromatic aliphatic or polyalkyloxyalkyl radical comprising about 6 to about 24 carbons, preferably 8 to 18 carbons. Such alkyl(alkyl glycosid)uronates have a balanced combination of a long and short alkyl chain which are surprisingly stable to enzyme hydrolysis.

Suitable mono-, oligo- or polysaccharides that may be used to form alkyl(alkyl glycosid)uronates of the invention include, but are not limited to glucose, galactose, mannose, gulose, sucrose, lactose, fructose, sorbitol, maltose and starch.

Examples of polyuronic acids, uronic acids or their lactones which may be used to form alkyl(alkyl glycosid)uronates of the invention include, but are not limited to D-glucuronic acid, D-glucurono-6,3-lactone and D-galacturonic acid. Other examples include D-mannuronic acid, L-guluronic acid, L-lyxuronic acid, L-Iduronic acid, pectin, algin, alginic acid, oxidized starch, oxidized cellulose and acacia.

Suitable aliphatic hydrocarbon radicals include saturated and unsaturated radicals including but not limited to methyl, ethyl, amyl, hexyl, heptyl, nonyl, decyl, undecyl, dodecyl, tridecyl, tetradecyl, pentadecyl, hexadecyl, heptadecyl and octadecyl; allyl, decenyl, dodecenyl, tetradecenyl, oleyl, linoleyl and linolenyl. The active compounds of the invention may contain straight or branched aliphatic groups. Aromatic radicals are exemplified by benzyl, aniline or substituted benzyl or aniline groups. Suitable mixed aliphatic aromatic groups are exemplified by benzylpropyl, phenylethyl, phenoxyethyl and vinylbenzyl. Cycloaliphatic radicals are exemplified by but not limited to cyclopentyl and cyclohexyl.

In one embodiment of the invention, an enzymatically stable mixed chain alkyl(alkyl glycosid)uronate is used as a surfactant in a novel detergent composition. An example of a specific mixed chain alkyl(alkyl glycosid)uronate is set forth below:

Mixed Chain alkyl(alkyl D-galactosid)uronate

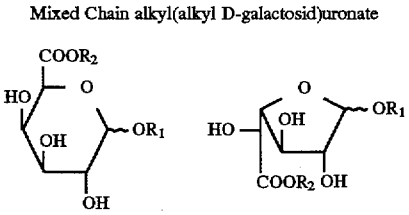

wherein, in each case, $R_2$ is a substituted or unsubstituted, saturated or unsaturated alkyl group having 6–24 carbons, preferably 8 to 18 carbons;

$R_1$ is hydrogen, a straight or branched chain alkyl group having 1 to 6 carbons, preferably 1 to 3 carbons or an alkenyl group having 2 to 6 carbons;

$R_2$ may also be an alkoxylated alkyl chain and the alkyl(alkyl D-glycosid)uronates may be ethoxylated and propoxylated or mixtures thereof.

It should be understood that $R_2$ may be defined as $R_1$ and $R_1$ as $R_2$ except that one has to be a short alkyl chain group with maximum 6 carbons and the other has to be a longer alkyl chain group.

The mixed chain alkyl(alkyl glycosid)uronates of the invention were found to be surprising hydrolytically stable to enzymes such as lipase. This is unusual because most sugar esters are generally sensitive to enzymes and hydrolyze readily. Because of their enzymatic stability and favorable surfactant properties, mixed chain alkyl(alkyl glycosid)uronates are well suited for detergent, personal product, cosmetic, pharmaceutical and dental applications, particularly enzyme containing powdered, light or heavy-duty liquid detergent compositions.

Examples of powdered detergent compositions are described in U.S. Pat. No. 4,929,379 to Oldenburg et al., and examples of light-duty liquid detergent compositions are described in U.S. Pat. No. 4,671,894 to Lamb et al., U.S. Pat. No. 4,368,146 to Aronson et al., and U.S. Pat. No. 4,555,360 to Bissett et al., all of which are hereby incorporated by reference into the subject application.

Examples of a heavy-duty liquid detergent composition are described in U.S. Pat. No. 4,959,179 to Aronson et al., which is hereby incorporated by reference into the subject application.

An ideal powdered detergent composition comprises the following (all percentage by weight):
(1) 1–40% mixed chain alkyl(alkyl glycosid)uronate
(2) 5–40% detergent active
(3) 0–50% builder or sequestering agent
(4) 0–40% buffering agent
(5) 0–30% electrolyte
(6) 0–20% bleach system
(7) 0.1–5% enzyme
(8) Balance minors plus water to 100%

Powdered detergent compositions of the invention can comprise from 1–60% mixed chain alkyl(alkyl glycosid)uronate, preferably 1–40%; from 5–70% detergent active; preferably 5–40%; from 0–70% builder, preferably 0–50%; from 0–60% buffering agent, preferably 0–40%; from 0–50% electrolyte, preferably 0–30%; from 0–30% bleach, preferably 0–20%; from 0–10% enzyme, preferably 0.1–5% and the balance minors or water.

An ideal liquid detergent composition comprises the following (all percentage by weight):
(1) 1–50% mixed chain alkyl(alkyl glycosid)uronate
(2) 5–70% detergent active
(3) 0–20% builder or sequestering agent
(4) 0–15% electrolyte
(5) 0.1–5% enzyme
(6) 0.1–15% enzyme stabilizer
(7) 0–20% phase regulant
(8) Balance minors plus water to 100%

Liquid detergent compositions of the invention can be built or unbuilt and may be aqueous or nonaqueous. The compositions generally comprise from 1–70% mixed chain alkyl(alkyl glycosid)uronate, preferably 1–50%; from 5–80% detergent active, preferably 5–70%; from 0–50% builder, preferably 0–20%; from 0–60% electrolyte, preferably 0–15%; from 0–10% enzyme, preferably 0.1–5%; from 0.1–30% enzyme stabilizer, preferably 0.1–15%; from 0–30% phase regulant, preferably 0–20% and the balance or water.

Suitable detergent actives of the invention that can be used are $C_{10}$ to $C_{24}$ carbon atom fatty acid soaps or anionic, nonionic, cationic, zwitterionic or amphoteric synthetic surfactants, or mixtures thereof, however, anionic and nonionic synthetic surfactants are preferred.

Examples of anionic synthetic surfactants that can be used are salts (including sodium, potassium, ammonium and substituted mono-, di-, and triethanolamine salts) of 8 to 20 carbon alkyl benzene sulfonates, 8 to 20 carbon primary or secondary alkanesulphonates, 8 to 20 carbon olefinsulphonates, 8 to 20 carbon alkylsulphates, 8 to 20 carbon alkylpolyglycolethersulfates and carboxylates containing up to 12 ethylene oxide units. Any suitable anionic surfactant may be used, however 8 to 20 carbon alkyl benzenesulfonates and primary alkanesulphonates are preferred.

Examples of nonionic synthetic surfactants that can be used are condensation products of ethylene oxide and propylene oxide with 8 to 20 carbon alcohols, 8 to 20 carbon alkylphenols or 8 to 20 carbon fatty acid amides. Any suitable nonionic surfactant may be used, however, 8 to 20 carbon ethoxylated alcohol containing 3 to 12 ethylene oxide units are preferred.

Builders that can be used according to this invention include conventional alkaline detergency builders, inorganic or organic.

Examples of suitable inorganic alkaline detergency builders are water-soluble alkalimetal phosphates, polyphosphates, borates, silicates and carbonates.

Examples of suitable organic alkaline detergency builders are polycarboxylate builders such as water-soluble salts of citric acid, mettitic acid, carboxymethyloxysuccinic acid and salts of polymers of itaconic acid and maleic acid. Other polycarboxylate builders include DPA (diplcolinic acid) and ODS (oxydisuccinic acid). Zeolites and aluminosilicates of the formula $Na_x((AlO_2)y \cdot (SiO_2)_y)ZH_2O$ wherein X and Y are integers of at least 6 and Z is an integer from about 15 to 264, for example, may be suitably used. Any suitable builder may be used, however, zeolites are preferred.

The alkaline buffering agent can be any such agent capable of providing a 1% product solution with a pH above 9. Advantageous alkaline buffering agents are the alkali metal silicates, since they decrease the corrosion of metal parts in washing machines and sodium metasilicate is preferred.

The liquid detergent compositions may comprise an amount of electrolyte (defined as a water-soluble salt) whose quantity depends on whether or not the composition is structured. By structured is meant the formation of lamellar phase sufficient to endow solid suspending capability.

The water-soluble electrolyte salt may be a detergency builder, such as sodium tripolyphosphate on it may be a non-functional electrolyte such as sodium sulfate or sodium chloride. Preferably, whatever builder is used in the composition comprises all or part of the electrolyte.

Enzymes which can be used are proteases, lipases, anylases, cellulases, oxidases, or mixtures thereof.

Stabilizers or stabilizer systems may be used in conjunction with enzymes may comprise of calcium chloride, calcium acetate, propionic acid salt, boric acid, boric oxide, borax, alkalimetal borates (e.g., sodium ortho-, meta- and pyroborate) or polyols such as propylene glycol, ethylene glycol, glycerol, sorbitol mannitol and glucose.

An especially preferred stabilization system is boric acid in combination with a polyol. Preferably, the weight ratio of polyol to boric acid added is at least one, more preferably at least about 1.3.

In addition to the ingredients described hereinbefore, the preferred compositions frequently contain a series of optional ingredients which are used for the known functionality in conventional levels. While the detergent compositions are generally premised on aqueous, enzyme-containing detergent systems, it is frequently desirable to use a phase regulant. This component, together with water, constitutes then the solvent matrix for the claimed liquid compositions. Suitable phase regulants are well-known in liquid detergent technology and can be represented by hydrotropes such as salts of alkylarylsulfonates having up to three carbon atoms in the alkyl group, e.g., sodium, potassium, ammonium and ethanolamine salts of xylene-, toluene-, ethylbenzene-, cumene-, and isopropylbenzene sulfonic acids. Alcohols may also be used as phase regulants. This phase regulant is frequently used in an amount from about 0.5% to about 20%, the sum of phase regulant and water is normally in the range from 35% to 65%.

Examples of oxygen or chlorine liberating bleaches that may be used are dichlorocyanuric acid salts or alkalimetal hypochlorides.

The preferred compositions herein can contain a series of further optional ingredients which are mostly used in minor additive levels, usually below about 5%. Examples of the like additives include: suds regulants; lather depressants; opacifiers; antioxidants; bactericides; germicides; optical brighteners; anti-tarnishing agents; dyes; fabric softening agents and perfumes.

In the second embodiment of the invention, a new process for the manufacture of surface active alkyl(alkyl glycosid) uronate is described.

It has been found, in accordance with the present invention, that non-surface active uronic acid esters or their lactones may undergo alkaline transesterification with higher alcohols ($C_6$–$C_{24}$) to produce surface active alkyl (alkyl glycosid)uronates. The invention can be more readily understood when reference is made to the general equation.

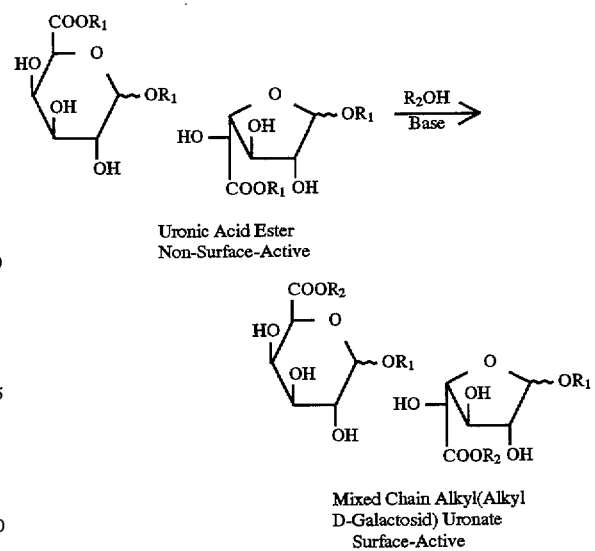

Uronic Acid Ester
Non-Surface-Active

Mixed Chain Alkyl(Alkyl D-Galactosid) Uronate
Surface-Active

The method of the invention is especially suitable for the manufacture of alkyl(alkyl glycosid)uronates wherein $R_1$ is hydrogen, a straight or branched chain alkyl group having 1 to 6 carbons, preferably 1 to 3 carbons or an alkenyl group with 2 to 6 carbons. $R_2$ is a straight or branched chain alkyl or alkenyl group which may contain an aromatic, cycloaliphatic, mixed aromatic aliphatic or polyalkyloxyalkyl radical comprising about 6 to 24 carbons, preferably 8 to 18 carbons.

The alcohol ($R_2OH$) can be used in stoichiometric molar amounts with respect to uronic acid ester or uronolactone. Preferably, however, as seen in Examples 1 through 5, it is added in excess. More preferably, the molar ratio of alcohol ($R_2OH$) to uronic acid ester or uronolactone is about 1.1:1 to 30:1, most preferably about 1.5:1 to 15:1. It is desirable to use water free reaction components, although small amounts of water can be tolerated.

In the process of the invention, the alcohol ($R_2OH$) can be added progressively, but is usually added in full amount at the beginning of the reaction and preferably in excess, but at least in a molar ratio of 1.5:1 to 15:1 with respect to uronic acid ester or uronolactone used.

The uronic acid ester or uronolactone used in the method of the invention is preferably in fine powder form, however, crystalline solids, flakes and syrups can be used as well. The reaction is performed at elevated temperature 30° C.–180° C., preferably 80° C.–130° C.

The reaction can be carried out under reduced pressure, however, it is preferably carried out at normal atmospheric pressure until the uronic acid ester or uronolactone has completely dissolved, then under reduced pressure to remove alcohol ($R_1OH$ and excess $R_2OH$).

The reactants are reacted preferably with intensive stirring for several hours, (e.g., 1 to 20 hours), preferably, however, until the uronic acid ester or uronolactone has completely dissolved which is about 2 to 10 hours.

The catalyst used to accelerate the rate of reaction are generally classified as Bronstead bases such as sodium hydroxide, potassium hydroxide, sodium metal, potassium metal or alkyl alkoxides such as sodium methoxide, potassium ethoxide, sodium decoxide and potassium dodecoxide. Any alkaline catalyst can be used, however, sodium metal and alkyl alkoxides are preferred. The catalyst can be added at any time during the reaction, however, it is preferably added at the beginning of the reaction followed by addition of uronic acid ester. The molar ratio of uronic acid ester to alkaline catalyst is about 100:1 to 1:1, preferably about 50:1 to 5:1, more preferably about 35:1 to 10:1.

In general, the surface additive alkyl(alkyl glycosid) uronates of the invention may be isolated as syrups, especially when derived from a mixture of anomers, however, crystalline solids are preferred and organic solvents may be optionally added to enhance crystallization. Typical organic solvents that may be used include, but are not limited to methanol, ethanol, propanol, isopropanol, butanol, acetonitrile, acetone, ethyl ether, petroleum ether, dioxane, tetrahydrofuran, chloroform, hexane, heptane, octane, decane, toluene and the like, however, acetonitrile, acetone, hexane and heptane are the preferred solvents. Mixtures of solvents can also be used.

The alkyl(alkyl glycosid)uronates prepared by the method of the invention are of high purity having a purity range of 93%–99%.

Because of their high degree of purity and good surfactant properties, they are well suited for use as biodegradable mild surfactants for detergent, personal product, cosmetic, pharmaceutical and dental applications such as powdered, light or heavy-duty liquid detergent compositions, bar compositions, shampoo compositions, conditioner compositions, shower gel compositions, bubble bath compositions, lotions, mouthwash compositions or dentifrice compositions and the like.

In order to more fully illustrate the nature of the invention and the manner of practicing the same, the following examples are presented. These examples are for illustrative purposes only and are not intended to be limiting in any way.

EXAMPLE 1

Preparation of Hexyl(Methyl α-D-Galactopyranosid)uronate (HMαGalp)

Methyl(methyl α-D-galactopyranosid)uronate (5.0 g, 0.023 mole) and a solution of anhydrous 1-hexanol (29.3, 0.29 mole) containing sodium metal (0.025 g, 0.0011 mole) were placed in an oven dried three-necked round bottom flask equipped with a mechanical stirrer, thermometer and short path distillation head. The mixture was heated at 80°–110° C. under a mild nitrogen blanket. After all had dissolved, methanol and excess 1-hexanol were removed by vacuum distillation. The resulting syrup was cooled, heptane (80 ml) added and stirred rapidly. The solution was then filtered, washed with heptane (3×30 ml) and recrystallized from water. The yield was 5.4 g (82.1%), MP 136°–137° C., Purity 99.2%.

EXAMPLE 2

Preparation of Octyl(Methyl α-D-Galactopyranosid) uronate (OMαGalp)

Prepared according to the procedure described for HMαGalp except anhydrous 1-octanol was used. The yield was 5.6 g (77.7%), MP 131°–132° C., Purity 98.9%.

EXAMPLE 3

Preparation of Decyl(Methyl α-D-Galactopyranosid)uronate (DMαGalp)

Prepared according to the procedure described for HMαGalp except anhydrous 1-decanol was used. The yield was 5.7 g (72.7%), MP 126°–127° C., Purity 98.4%.

EXAMPLE 4

Preparation of Decyl(Methyl β-D-Galactopyranosid)uronate (DMβGalp)

Prepared according to the procedure described for HMαGalp except methyl(methyl β-D-galactopyranosid) uronate and anhydrous 1-decanol were used. The yield was 5.5 g (70.0%), MP 106°–107° C., Purity 93.3%.

EXAMPLE 5

Preparation of Dodecyl(Methyl α-D-Galactopyranosid)uronate (DoMαGalp)

Prepared according to the procedure described for HMαGalp except 1-dodecanol was used. The yield was 7.9 g (91.2%), MP 121°–122° C.

SURFACTANCY

In order to demonstrate the effectiveness of these compounds as effective surfactants, especially in enzyme containing detergent compositions, various physical properties such as enzyme stability and detergency were measured.

EXAMPLE 6

Enzyme Stability

Enzyme catalyzed hydrolysis of uronates was monitored using a TitraLab (Radiometer, Copenhagen) pH-stat autotitrator. Emulsified substrate was prepared by mixing water (5 mL), 1-butanol (1 mL), acacia gum (1 g), and substrate (0.357 mmoles) using a homogenizer (Omni-mixer, OCI Instruments) for 15 minutes. Emulsified substrate (5 mL) was mixed with Tris-HCl buffer (20 mL, 100 mM, pH 8.0) and equilibrated at 30° C. in a thermostatic reaction cup. Lipolase (20.5 LU) was added to initiate the reaction and the production of acid was monitored by titration with 0.1N NaOH.

| COMPOUND | MEAN SLOPE | REL VELOCITY | STABILITY |
|---|---|---|---|
| α-Methyl D-Glucose Monolaurate | 3.9921 | 100 | 1X |
| D-Glucose Monolaurate | 1.6880 | 42 | 2.4X |
| Decyl (Methyl β-D Galactopyranosid)-uronate | 0.7101 | 18 | 5.6X |
| Hexyl (Methyl α-D | very stable/slow hydrolysis | | |

| COMPOUND | MEAN SLOPE REL VELOCITY STABILITY |
|---|---|
| Galactopyranosid)-uronate | 5 |

As can be seen from the table above, lipolase hydrolyzes α-methyl D-glucose monolaurate and D-glucose monolaurate more quickly than decyl(methyl β-D-galactopyranosid) uronate or hexyl(methyl α-D-galactopyranosid)uronate. This finding is unexpected since mixed chained alkyl(alkyl D-glycosid)uronates of the invention have very similar structures to that of α-methyl D-glucose monolaurate and D-glucose monolaurate. This test suggests that the mixed chain alkyl(alkyl glycosid)uronates are surprising enzymatically stable.

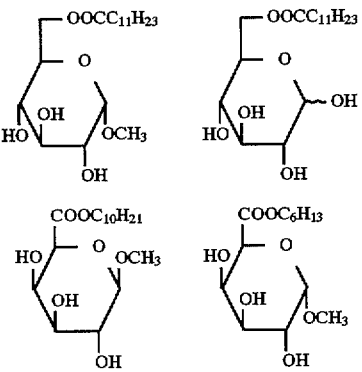

EXAMPLE 7

Wash Cycle Stability (t½)

The wash cycle stability or half-life (t½) of decyl(methyl α-D-galactopyranosid)uronate was determined using an automatic titrator at 40° C., pH=10, $8.13 \times 10^{-3}$M concentration.

| COMPOUND | (t½) |
|---|---|
| Decyl(methyl α-D-galactopyranosid)uronate | 7.9 hrs. |

This finding suggests that Decyl(methyl α-D-galactopyranosid)uronate is hydrolytically stable enough for a typical wash cycle at elevated temperatures.

EXAMPLE 8

Detergency Evaluation (Prototype Detergent Formulation)

The detergency performance of decyl(methyl α-D-galactopyranosid) uronate was evaluated on WFK 30D cloth (polyester cloth coated with pigment/sebum) using a tergotometer. The performance of decyl(methyl α-D-galactopyranosid)uronate was evaluated as a mixed system (70:22.5:7.5, 70:15:15, 70:7.5:22.5 LAS:Neodol 25-7:Uronate) at about 0.22 g/L total surfactant. A nonphosphate, zeolite-built burkite base powder was dosed over the side at about 0.75 g/L. The ratio of total surfactant to zeolite burkite base powder was 21.6%:78.4%. The system was kept at 37° C., pH=10, 120 ppm hardness for 15 minutes. The detergency improvement was measured by a change in reflectance (ΔR) of the stained cloth before and after washing with the detergent prototype as measured in a standard reflectometer. In general, larger reflectance values suggest better detergency and oily soil removal.

The prototype detergent composition is as follows:

| INGREDIENTS | WEIGHT % |
|---|---|
| Linear Alkylbenzenesulfonate (LAS) | 1–40 |
| Alkyl(Alkyl D-Glycosid)uronamide | 1–40 |
| Neodol 25-7 | 1–40 |
| Zeolite Burkite Base Powder | 10–97 |

Neodol 25-7 is an alkoxylated nonionic surfactant having an average degree of alkoxylation of about 7 and an average chain length of about $C_{12}$–$C_{15}$.

The detergency performance of decyl(methyl α-D-galactopyranosid) uronate is set forth below:

| Surfactant Ratios = LAS:Neodol 25-7:Uronate (21.6% by weight total active) | ΔR |
|---|---|
| 100:0:0 | 11.8 |
| 70:30:0 | 11.5 |
| 70:22.5:7.5 | 14.7 |
| 70:15:15 | 14.0 |
| 70:7.5:22.5 | 13.3 |
| 70:0:30 | 6.8 |
| 0:0:0 | 1.3 |

As seen from the above table, the addition of from about 5% to about 25% uronate to a mixture of LAS and Neodol 25-7 (70:22.5:7.5, 70:15:15 and 70:7.5:22.5) unexpectedly results in synergistic enhanced oily soil removal compared to either a mixture of LAS and Neodol 25-7 (70:30:0) or LAS alone (100:0:0). The detergency data, suggests that mixed chain alkyl(alkyl D-glycosid)uronates of the invention provide synergistic detergency when mixed with anionic surfactants or nonionic surfactants or both.

It should be understood that the specific forms of the invention herein illustrated and described are intended to be representative only. Changes, including but not limited to those suggested in this specification, may be made in the illustrated embodiments without departing from the clear teachings of the disclosure accordingly, reference should be made to the following appended claims in determining the full scope of the invention.

What is claimed is:

1. A mixed chain alkyl(alkyl glycosid)uronate compound having the formula:

Mixed Chain alkyl(alkyl D-galactosid)uronate

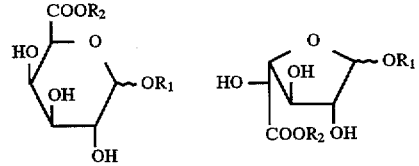

wherein:

$R_2$ is a substituted or unsubstituted, saturated or unsaturated alkyl group having 6 to 24 carbons; and $R_1$ is hydrogen, a straight or branched chain alkyl group having 1 to 6 carbons or an alkenyl group having 2 to 6 carbons.

2. A detergent composition comprising the compound of claim 1.

3. A liquid detergent compositions according to claim 1 comprising (all percentages by weight):
  (1) 1–50% mixed chain alkyl(alkyl glycosid)uronate
  (2) 5–70% detergent active
  (3) 0–20% builder or sequestering agent
  (4) 0–15% electrolyte
  (5) 0.1–5% enzyme
  (6) 0.1–15% enzyme stabilizer
  (7) 0–20% phase regulant
  (8) Balance minors plus water to 100%.

4. A powdered detergent composition according to claim 1 comprising (all percentages by weight):
  (1) 1–40% mixed chain alkyl(alkyl glycosid)uronate
  (2) 5–40% detergent active
  (3) 0–50% builder or sequestering agent
  (4) 0–40% buffering agent
  (5) 0–30% electrolyte
  (6) 0–20% bleach system
  (7) 0.1–5% enzyme
  (8) Balance minors plus water.

5. A process for making the compound of claim 1 which process comprises combining an alcohol $R_2OH$ with a uronic acid ester or uronolactone as set forth below:

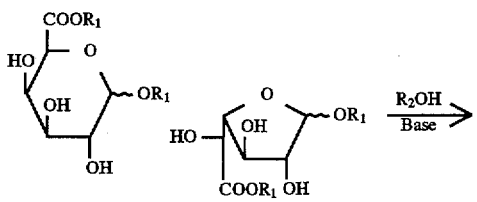

Uronic Acid Ester
Non-Surface-Active

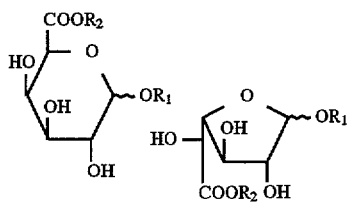

Mixed Chain Alkyl(Alkyl D-Galactosid) Uronate
Surface-Active wherein:

$R_1$ is hydrogen, a straight or branched alkyl group having 1 to 6 carbonss or alkenyl group having 2 to 6 carbons and $R_2$ is a substituted or unsubstituted, saturated or unsaturated alkyl group having 6 to 24 carbons wherein the ratio of alcohol to uronic acid ester or uronolactone is from 1:1 to 30:1;

said reaction being carried out in about 1 to 20 hours at about 30° C. to about 180° C. in the presence of a base catalyst.

6. A process according to claim 5, wherein said catalyst is a Bronstead base.

7. A process according to claim 5, wherein the ratio of uronic acid ester to catalyst is from about 100:1 to 10:1.

* * * * *